United States Patent [19]
Brown et al.

[11] Patent Number: 5,278,999
[45] Date of Patent: Jan. 18, 1994

[54] COMBINED EAR AND EYE PROTECTION DEVICE

[76] Inventors: Ronald Brown, 8600 Woodway, #379, Houston, Tex. 77063; Kenneth B. Forsyth, 14547 Chadbourne, Houston, Tex. 77079

[21] Appl. No.: 18,115

[22] Filed: Feb. 17, 1993

[51] Int. Cl.⁵ .................. A61F 9/02; G02C 3/02; G02C 11/00
[52] U.S. Cl. .................................... 2/209; 2/6.3; 2/10; 351/118; 351/155; 351/158
[58] Field of Search ............... 2/209, 6, 423, 10, 9, 2/6.3; 351/158, 155, 116, 118

[56] References Cited

U.S. PATENT DOCUMENTS

| | | | |
|---|---|---|---|
| 1,621,629 | 3/1927 | Dawson | 351/158 X |
| 3,871,372 | 3/1975 | Bivins | |
| 3,943,574 | 3/1976 | Yamaguchi et al. | 2/209 X |
| 3,943,925 | 3/1976 | Leight | |
| 4,572,323 | 2/1986 | Randall | |
| 4,856,086 | 8/1989 | McCullough | |
| 4,856,089 | 8/1989 | Horton | |
| 4,902,120 | 2/1990 | Weyer | |
| 5,009,496 | 4/1991 | Holtan, Jr. et al. | |
| 5,133,596 | 7/1992 | Korny et al. | 351/158 |
| 5,179,736 | 1/1993 | Scanlon | 2/209 |

Primary Examiner—Peter Nerbun
Attorney, Agent, or Firm—Pravel, Hewitt, Kimball & Krieger

[57] ABSTRACT

An improved combined ear and eye protector is disclosed which provides optimum flexibility by permitting the use of both eye and ear protection, or alternatively eye protection only or ear protection only. Maximum flexibility is achieved by providing an ear protection system which includes a head support independent of the eye protector.

9 Claims, 3 Drawing Sheets

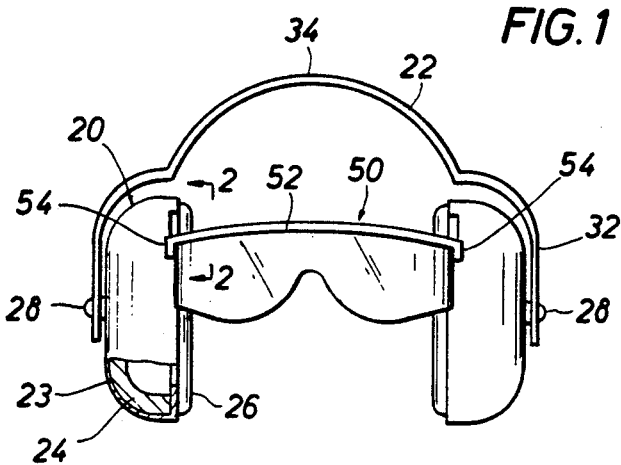
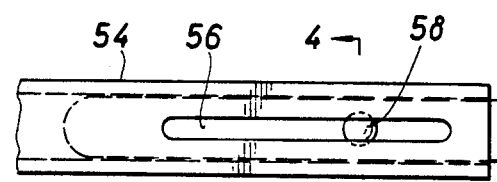
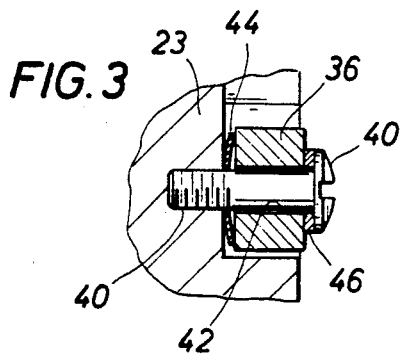
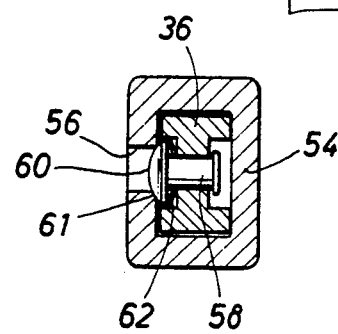
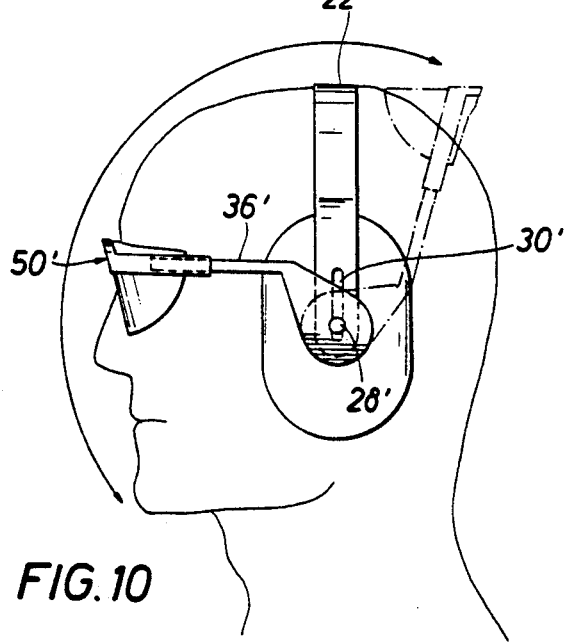
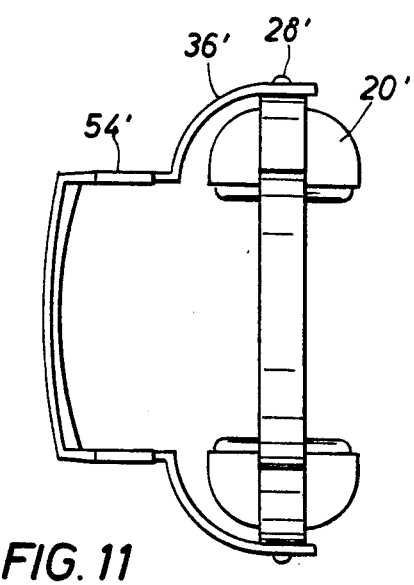

COMBINED EAR AND EYE PROTECTION DEVICE

BACKGROUND OF THE INVENTION

1. Field of the Invention

The present invention relates to an improved combined ear and eye protection device for use wherever ear and sight protection are necessary. More specifically, the invention relates to an improved ear and eye protector which permits the user to employ either eye protection or ear protection or both. Further, the eye protector may be removed and alternate designs used depending on the needs of the user.

1. Description of the Prior Art

The need exists for an improved ear and eye protection device which is comfortable, functional and aesthetically pleasing. It is not uncommon in many industries, such as ground aviation maintenance, for employees to use ear and eye protection. In some cases, federal and/or state regulations, or company policies, require the use of ear and eye protection. If such devices could be combined into a single functional assembly, the advantages are apparent.

Heretofore, however, efforts to combine an ear and eye protection device has been met with limited success primarily because of the difficulties associated with the user trying to discontinue the use of eye protection temporarily but maintaining ear protection or vice versa.

While there are devices which can function both for hearing and sight protection, such devices are uncomfortable, or have failed to provide adequate flexibility in selecting either eye or ear protection temporarily. See for example, Horton, U.S. Pat. No. 4,856,059; and Leight, U.S. Pat. No. 3,943,925.

Further, the need exists for a combined ear and eye protection device which provides the added flexibility of enabling the user to substitute alternate eye protection depending on the user's needs.

SUMMARY OF THE INVENTION

Briefly, the invention relates to an improved combined ear and eye protection device. The ears are protected by ear muffs or coverings having an exterior housing with interior sound absorbent material. The ear muffs are designed to fit over the ears of the user. A headband is attached at each end to an ear muff and is adapted to fit over the head of the user thereby laterally restraining the ear muffs and also providing vertical support for both the ear muffs and the eye protector. An eye protector is then separately attached through a pivotal connection directly to the ear muffs. In this manner, the ear muffs are structurally supported over the user by a separate headband and the eye protection is pivotally attached to the ear muffs. This enables the user to rotate the eye protector out of the way without affecting the position of the ear muffs. Alternatively, the ear muffs may be rotated slightly to enable normal hearing yet maintaining the position of the eye protector for continued eye protection. Further, the entire unit may be lowered to the base of the neck without discomfort for temporarily discontinuing ear and eye protection.

Moreover, the frontal frame portion of the eye protector is removable from at least a portion of the temples enabling the user to substitute other types of eye protectors for different applications.

The more important features of this invention have been summarized rather broadly in order that the detailed description may be better understood. There are, of course, additional features of the invention which will be described hereafter and which will also form the subject of the claims appended hereto.

BRIEF DESCRIPTION OF THE DRAWINGS

In order to more fully describe the drawings used in the detailed description of the present invention, a brief description of each drawing is provided.

FIG. 1 is a front elevation view of the present invention.

FIG. 2 is a cross-sectional detail view taken along line 2—2 of FIG. 1.

FIG. 3 is a cross-sectional detail view taken along line 3—3 of FIG. 2.

FIG. 4 is a cross-sectional view taken along line 4—4 of FIG. 2.

FIG. 10 is a side elevation view of an alternate embodiment of the present invention.

FIG. 11 is a top view of the alternate embodiment of the present invention.

DETAILED DESCRIPTION OF THE PRESENT INVENTION

Figure 5:
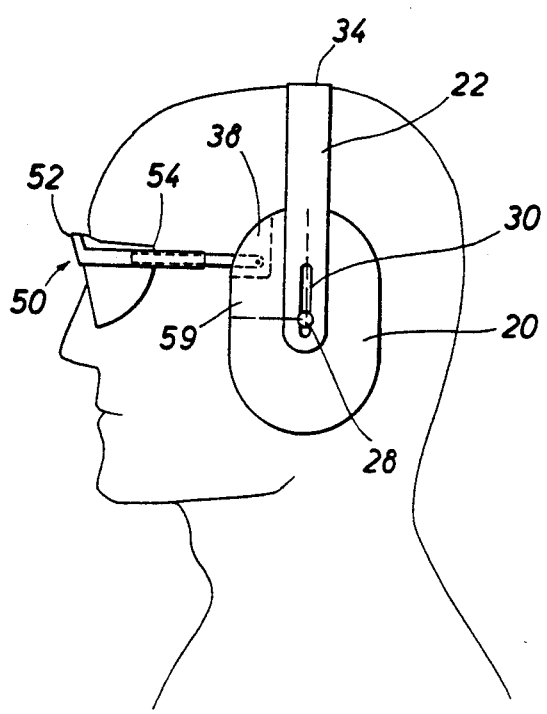
FIG. 5 is a side view of the present invention with the eye protector and the ear protectors in normal position for maximum protection.

Referring to FIGS. 1-5 and more particularly FIGS. 1 and 5, the combined ear and eye protection device is shown having a pair of ear muffs or coverings 20 pivotally attached to a headband 22. Each ear muff comprises an outer shell 23 with an interior sound absorbent material 24. A seal 26 is located on the inside surface of each ear muff. The ear muffs 20 are adjustably mounted on the band 22 by means of a notched pin 28 which slides within a slot 30 on the lower portion 32 of the headband 22. In this manner, the ear muffs may be positioned over the user and the headband adjusted so that the top 34 of the headband 22 fits against the head of the user. A more detailed description of the assembly and construction of the ear muffs and headband as discussed above is set forth in U.S. Pat. No. 4,572,323, which disclosure is hereby incorporated by reference and made a part of this disclosure.

Still referring to FIGS. 1-5 and more particularly FIGS. 2-4, the present invention includes a pivotal hinge 36 which is preferably attached to the interior of the shell 23 of each ear muff. More preferably, the hinge 36 is attached to the shell 23 within a recessed region 38. The hinge is used to attach and assist in the rotation of eye protector 50. As shown in FIG. 3, a screw 40 which passes through aperture 42 of hinge 36 secures the hinge 36 to the ear muff 20. A spring 44 preferably is located between ear muff shell 23 and hinge 36 to create friction and hold eye protector 50 in an elevated position as will be discussed below. A washer 46 is located between the head of screw 40 and hinge 36 to permit rotation of hinge 36 without screw 40 prematurely unscrewing. Ergonomically, the hinge point (screw 40) preferably should be located within the top frontal quadrant 59 of shell 20 (see FIG. 5).

The eye protector 50 includes a frontal frame 52 and side templates 54. The side templates 54 are attached to the hinge 36 by a pin connection as shown in FIGS. 2 and 4. In the preferred embodiment, the template 54 includes a slot 56 in which a pin 58 is permitted to move. The head 60 of pin 58 is frictionally held against the covers 61 of slot 56 by a spring washer 62. In this manner, the position of the pin 58 is held fixed relative to the template until the user adjusts the distance of the eye protector from the ear muffs by pulling/pushing on the templates 54 relative to the hinge 36. By providing slots 30 and 56, maximum utility is achieved by satisfying various head sizes.

Templates 54 can be removed from hinge 36 by pushing down on head 60 of pin 58 and pulling the template off hinge 36. Thus, the eye protector 50 may be removed and a substitute eye protector connected, such as darker lenses for sun protection, amber lenses for target practice or other firearm activity, or other applications where other colors and shapes of eye protectors are desirable.

Referring now to FIGS. 5-8, the advantages of the present invention are further illustrated by depicting the various options which the present invention permits.

FIG. 5 shows the normal position of the present invention when both ear protection and eye protection are desirable.

Figure 6:
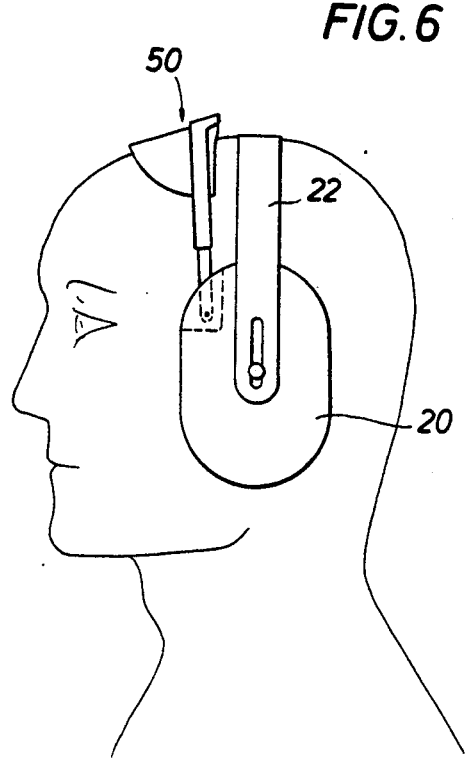
FIG. 6 is a side view of the present invention with the eye protector raised but the ear protectors in place.

In FIG. 6, the eye protector 50 has been raised, but the ear protection remains in place. This is possible because slot 56 on templates 54 permits the extension of the eye protector enabling the user to lift the eye protector above his eyebrows and place it on his forehead or upper part of the head. As can be seen, by mounting the templates 54 to the ear muffs 20 through hinge 36 the flexing motion of the headband is not affected and ear muffs 20 remain securely in place.

Figure 7:
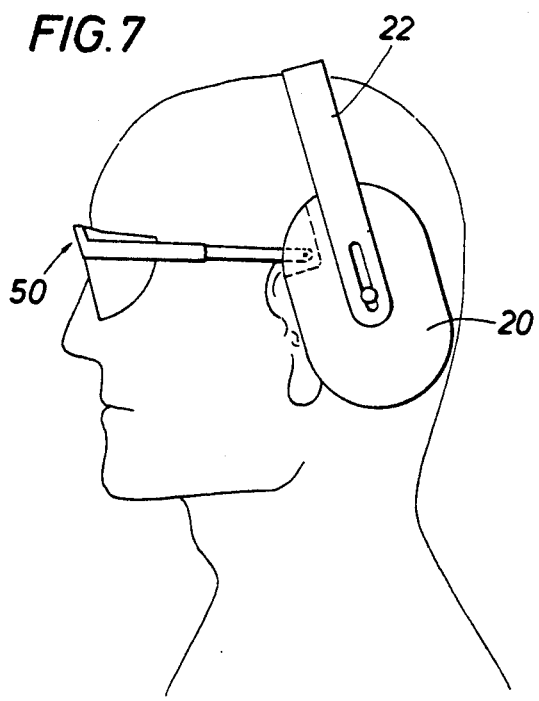
FIG. 7 is a side view of the present invention with the eye protector in place but the ear protectors displaced rearwardly.

FIG. 7 shows another position wherein the user continues to use eye protector 50 but has moved the ear muffs 20 backwards to permit normal hearing. Again, the invention permits such because of slot 56 permits the frontal frame 52 to rest on the nose of the user. Alternatively, the ear muffs may be slid forwardly to permit normal hearing while eye protector 50 remains in position because of slot 56.

Figure 8:
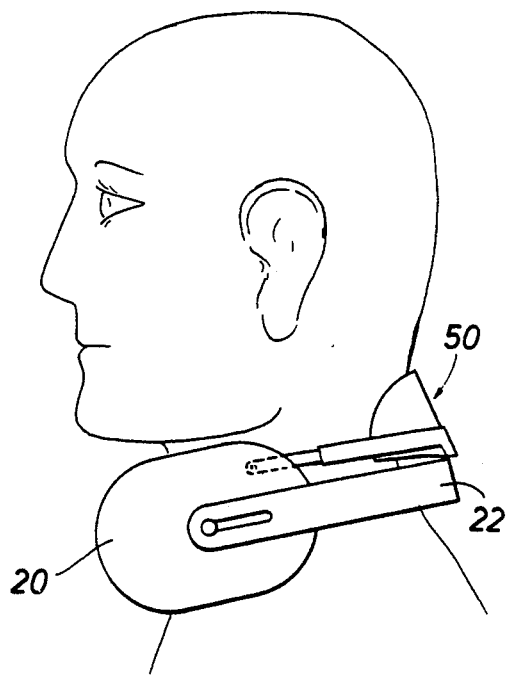
FIG. 8 is a side view of the present invention relocated to the base of the neck of the user.

Referring to FIG. 8, the present invention has been lowered to the base of the neck permitting the user to perform normal activities without eye or ear protection. Because of the pivotal connection of the hinge at screw 40 within the top frontal quadrant 59, eye protector 50 may be elevated and may rest at the base of the neck of the user juxtapose the headband 22 in a comfortable position.

Figure 9:
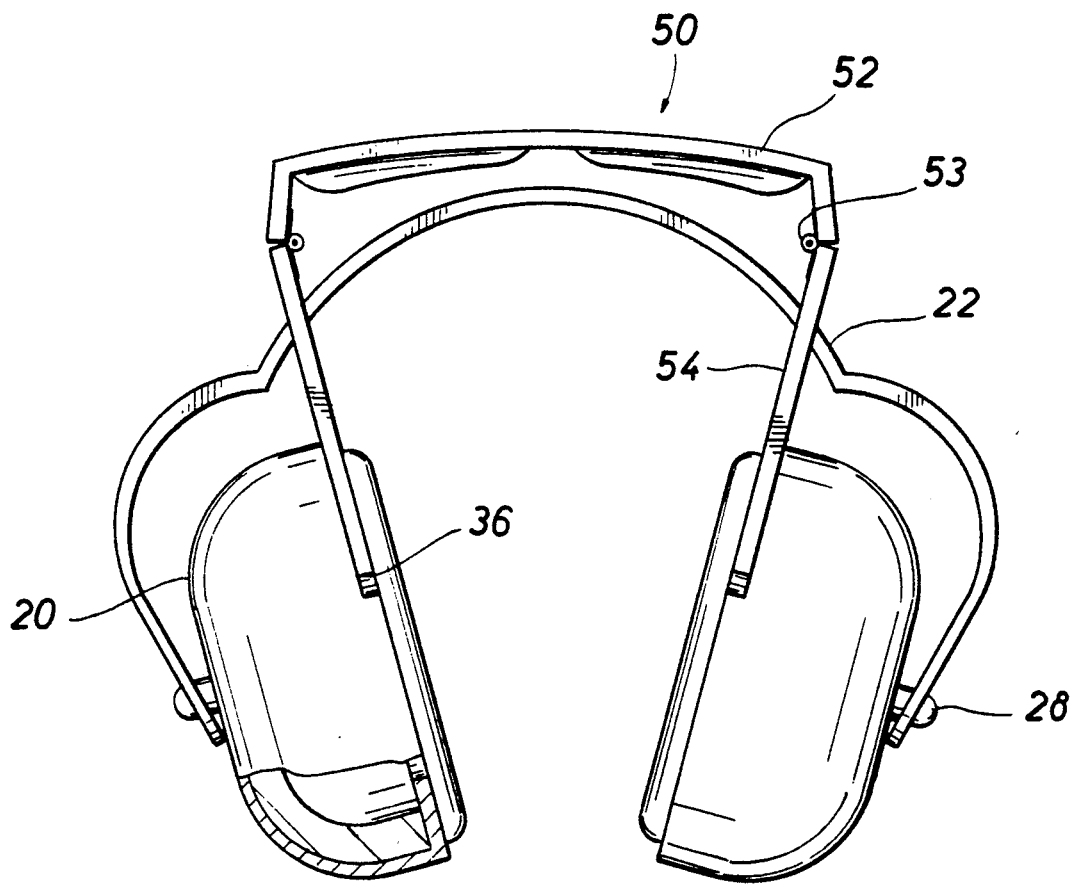
FIG. 9 is a front view of the present invention in a non-functioning or relaxed mode.

FIG. 9 shows the present invention in a relaxed mode as it would be at the base of the user's neck (FIG. 8). Since the eye protector 50 includes a hinge point 53 between the frontal frame 52 and the templates 54, the headband 22 may relax moving the ear muffs 20 inwardly without stressing the frontal frames 52. This permits a snug fit of the present invention around the base of the user's neck.

Referring now to FIGS. 10 and 11, an alternate embodiment of the present invention is shown. In the alternate embodiment, hinge 36' is pivotally attached at the center of the ear muff 20' through pin 28'. The hinge 36' includes an aperture through which pin 28' passes. Thus, eye protector 50'/hinge 36' may be moved vertically within slot 30' to adjust ear muffs 20' and eye protector 50' to the particular user.

Accordingly, eye protector 50' may be rotated more than 90° past the top of the band 22' as shown in FIG. 10 when not in use. Alternatively, eye protector 50' may be lowered in a counterclockwise direction as shown in FIG. 11 to a position below the chin of the user. The lateral displacement of eye protector 50' away from the user's face is possible through the use of a slot 56 and pin connection arrangement as shown in FIGS. 2 and 4 of the preferred embodiment.

Thus, even in the alternate embodiment as shown in FIGS. 10-11, the user may employ either an eye protector or the ear protectors in various combinations as shown in FIGS. 5-8 of the preferred embodiment.

The present invention has been described in terms of a preferred embodiment. Obviously, modifications and alterations to this embodiment will be apparent to those skilled in the art in view of this disclosure. For example, various hinges may be used to achieve the same purpose. Further, other variations of the template configuration will be apparent to those skilled in the art in view of this disclosure. For example, other designs are possible for the lateral displacement of the frontal frame relative to the template other than the use of a slot/pin connection as shown in FIGS. 2-4 in view of this disclosure to one skilled in the art. However, it is intended that all such variations and equivalent modifications fall within the spirit and scope of the present invention as claimed.

What is claimed is:

1. A combined ear and eye protection device comprising:
   a pair of ear muffs each having an exterior housing and interior sound absorbing material, each said muffs adapted to fit over one ear of the user;
   a headband adjustably attached at each end to one of said ear muffs and adapted to fit over the head of the user; and
   eye protector glasses having a front frame and two side templates, each template attached at one end to said frame and pivotally attached at its other end to said ear muffs, said templates including means for horizontal adjustment independently of said pivotal attachment to said ear muffs.

2. The combined ear and eye protection device according to claim 1, wherein said ear muffs include a top frontal quadrant and said pivotal attachment of said templates being located within the said quadrant.

3. The combined ear and eye protection device according to claim 1, wherein said front frame being removable from at least a portion of said templates thereby permitting the user to substitute frontal frames.

4. A combined ear and eye protection device comprising:
   a pair of ear muffs each having an exterior housing and interior sound absorbing material, each said muffs adapted to fit over one ear of the user;
   a headband adjustably attached at each end to one of said ear muffs and adapted to fit over the head of the user; and
   eye protector glasses having a front frame and two side templates wherein each template is attached at one end to said frame and pivotally attached at its other end to the interior of said ear muffs and said frame being removable from at least a portion of each said template permitting the substitution of alternate frames, said templates including means for horizontal adjustment independently of said pivotal attachment to said ear muffs;

wherein each ear muff includes a top frontal quadrant and said pivotal attachment of said templates being located within said quadrant.

5. The combined ear and eye protection device according to claim 4, wherein said ear muffs include an exterior and interior surface, said templates being pivotally attached to said interior surface of said top frontal quadrant of said ear muffs.

6. The combined ear and eye protection device according to claim 5, wherein said headband and said eye protector glasses are independently attached to said ear muffs so as to allow a first position wherein said eye protector glasses and said ear muffs are simultaneously being used as the protection device, a second position wherein only said ear muffs are being used as the protection device, and a third position wherein only said eye protector glasses are being used as the protection device while said headband is in place on the head of the user.

7. The combined ear and eye protection device according to claim 4, wherein said headband and said eye protector glasses are independently attached to said ear muffs so as to allow first position wherein said eye protector glasses and said ear muffs are simultaneously being used as the protection device, a second position wherein only said ear muffs are being used as the protection device, and a third position wherein only said eye protector glasses are being used as the protection device while said headband is in place on the head of the user.

8. The combined ear and eye protection device according to claim 1, wherein said headband and said eye protector glasses are independently attached to said ear muffs so as to allow a first position wherein said eye protector glasses and said ear muffs are simultaneously being used as the protection device, a second position wherein only said ear muffs are being used as the protection device, and a third position wherein only said eye protector glasses are being used as the protection device while said headband is in place on the head of the user.

9. A combined ear and eye protection device comprising:
- a pair of ear muffs each having an exterior housing and interior sound absorbing material, each said muffs adapted to fit over one ear of the user;
- a headband adjustably attached at each end to one of said ear muffs and adapted to fit over the head of the user; and
- eye protector glasses having a front frame and two side templates each template attached atone end to said frame and pivotally attached at other end to the interior of said ear muffs,
- said headband and said eye protector glasses being independently attached to said ear muffs so as to allow a first position wherein said eye protector glasses and said ear muffs are simultaneously being used as the protection device, a second position wherein only said ear muffs are being used as the protection device, and a third position wherein only said eye protector glasses are being used as the protection device while said headband is in place on the head of the user.

* * * * *

UNITED STATES PATENT AND TRADEMARK OFFICE
CERTIFICATE OF CORRECTION

PATENT NO. : 5,278,999
DATED : January 18, 1994
INVENTOR(S) : Ronald Brown and Kenneth B. Forsyth It is certified that error appears in the above-identified patent and that said Letters Patent is hereby corrected as shown below:

Col. 5, line 29 after "allow" insert --a--.

Col. 6, line 23 after "templates" insert --,--; and, delete "atone" and insert --at one--.

Col. 6, line 24 after "at" insert --its--.

Signed and Sealed this

Thirty-first Day of May, 1994

Attest:

BRUCE LEHMAN

Attesting Officer     Commissioner of Patents and Trademarks